United States Patent
Pronin et al.

(10) Patent No.: US 9,030,733 B2
(45) Date of Patent: May 12, 2015

(54) SPATIALLY RELAYING RADIATION COMPONENTS

(75) Inventors: Oleg Pronin, Garching (DE); Alexander Apolonskiy, Garching (DE); Ferenc Krausz, Garching (DE); Vladimir Pervak, Munich (DE)

(73) Assignees: Max-Planck-Gesellschaft zur Foerderung der Wissenschaften e.V., Munich (DE); Ludwig-Maximilians-Universitaet Muenchen, Munich (DE)

( * ) Notice: Subject to any disclaimer, the term of this patent is extended or adjusted under 35 U.S.C. 154(b) by 0 days.

(21) Appl. No.: 14/110,757

(22) PCT Filed: Apr. 5, 2012

(86) PCT No.: PCT/EP2012/001541
§ 371 (c)(1),
(2), (4) Date: Oct. 28, 2013

(87) PCT Pub. No.: WO2012/139744
PCT Pub. Date: Oct. 18, 2012

(65) Prior Publication Data
US 2014/0036352 A1  Feb. 6, 2014

(30) Foreign Application Priority Data
Apr. 12, 2011 (EP) .................................. 11003085

(51) Int. Cl.
*H01S 3/106* (2006.01)
*G02B 27/10* (2006.01)
(Continued)

(52) U.S. Cl.
CPC .............. *G02B 27/1006* (2013.01); *H01S 3/106* (2013.01); *G02B 5/283* (2013.01); *H01S 3/08059* (2013.01); *G01N 21/25* (2013.01); *H01S 3/08* (2013.01)

(58) Field of Classification Search
USPC .......................... 359/346, 328, 326; 372/2, 22
See application file for complete search history.

(56) References Cited

U.S. PATENT DOCUMENTS

| 6,147,806 A | 11/2000 | Park et al. |
| 2010/0007860 A1 | 1/2010 | Ueda et al. |

(Continued)

FOREIGN PATENT DOCUMENTS

| FR | 1049583 | 12/1953 |
| WO | 2008065204 A1 | 6/2008 |

(Continued)

OTHER PUBLICATIONS

Ashkin et al., "Resonant Optical Second Harmonic Generation and Mixing", IEEE Journal of Quantum Electronics, vol. QE-2, No. 6, pp. 109-124 (1966).

(Continued)

*Primary Examiner* — Mark Hellner
(74) *Attorney, Agent, or Firm* — Caesar, Rivise, Bernstein, Cohen & Pokotilow, Ltd.

(57) ABSTRACT

A method of spatially relaying a first radiation component (1) having a first wavelength and a second radiation component (2) having a second wavelength different from the first radiation component (1), using an optical relaying device (10) which comprises a transparent plate (11) having anti-reflection coatings (12, 13) on both side surfaces thereof, comprises transmitting the first radiation component (1) across the optical relaying device (10) with predetermined incident (α) and emergent angles (β), resp., wherein said anti-reflection coatings (12, 13) being effective for the first radiation component (1) at the incident and emergent angles (α, β), resp., and reflecting the second radiation component (2) at the optical relaying device (10) with a predetermined reflection angle (α) being equal to at least one of said incident and emergent angles (α, β), wherein the first and second radiation components (1, 2) are split from each other toward different directions or combined into a common beam path. Furthermore, an optical relaying device (10) and a resonator device, in particular enhancement cavity device (100) and a laser resonator, are described.

15 Claims, 4 Drawing Sheets

(51) Int. Cl.
*G02B 5/28* (2006.01)
*G01N 21/25* (2006.01)
*H01S 3/08* (2006.01)

(56) References Cited

U.S. PATENT DOCUMENTS

2011/0013653 A1* 1/2011 Krausz et al. ............... 372/22
2012/0154902 A1* 6/2012 Boullet et al. .............. 359/328

FOREIGN PATENT DOCUMENTS

WO 2009092600 A1 7/2009
WO 2010084202 A1 7/2010

OTHER PUBLICATIONS

Cingoez et al., "Power Scaling of High-Repetition-Rate HHG", International Conference on Ultrafast Phenomena, Optical Society of America (2010).
De Grazia et al., "Applications of intense ultra-short XUV pulses to solid state physics: Time-resolved luminescence spectroscopy and radiation damage studies", Proc. of SPIE, vol. 6586, pp. 658601-658610 (2007).
Eidam et al., "Femtosecond fiber CPA system emitting 830 W average output power", Optics Letters, vol. 35, No. 2, pp. 94-96 (2010).
Gohle et al., "A frequency comb in the extreme ultraviolet", Nature, vol. 436, No. 14, pp. 234-237 (2005).
Hansch et al., "Laser Frequency Stabilization by Polarization Spectroscopy of a Reflecting Reference Cavity", Optics Communications, vol. 35, No. 3, pp. 441-444.
Jones et al., "Phase-Coherent Frequency Combs in the Vacuum Ultraviolet via High-Harmonic Generation inside a Femtosecond Enhancement Cavity", Physical Review Letters, vol. 94, pp. 193201-1-4 (2005).
Potma et al., "Picosecond-pulse amplification with an external passive optical cavity", Optics Letters, vol. 28, No. 19, pp. 1835-1837 (2003).
Pupeza et al., "Power scaling of a high-repetition-rate enhancement cavity", Optics Letters, vol. 35, No. 12, pp. 2052-2054 (2010).
Yost et al., "Efficient output coupling of intracavity high-harmonic generation", Optics Letters, vol. 33, No. 10, pp. 1099-1101 (2008).
International Search Report for PCT/EP2012/001541 dated Jul. 18, 2012.

* cited by examiner ary active element (WO 2009/
SPATIALLY RELAYING RADIATION COMPONENTS

FIELD OF THE INVENTION

The present invention relates to a method of spatially relaying, in particular splitting or combining, radiation components with different wavelengths, like spatially relaying a first radiation component, which e.g. includes a fundamental wavelength in an optical wavelength range, and a second radiation component, which e.g. includes shorter wavelengths compared with the fundamental wavelength, in particular second or higher harmonic wavelengths relative to the fundamental wavelength. Furthermore, the present invention relates to a method of output coupling radiation from an optical resonator like e.g. an enhancement cavity or a laser resonator, to a method of conducting a pump-probe measurement, to an optical relaying device being capable of wavelength-selective relaying, in particular splitting or combining of radiation components, and to a resonator device, in particular an enhancement cavity or a laser resonator provided with the optical relaying device. Applications of the invention are available e.g. in the fields of operating high-power ultrafast laser sources.

PRIOR ART

Recent progress in the laser development paves new promising ways in many technological areas, like e.g. attosecond pulse generation, high resolution spectroscopy with XUV frequency combs, pump-probe measurements, photoelectron emission microscopy, photoelectron imaging spectroscopy (PEIS), nanostructure characterization, which could substantially benefit from XUV MHz-repetition-rate sources. A conventional method to generate XUV radiation is frequency conversion by focusing high energy femtosecond intense pulses into a target medium, wherein high peak intensities ($>10^{13}$ W cm$^{-2}$) are needed for this process.

The use of a high-finesse optical cavity (enhancement cavity) for coherent storage of radiation and creating intense pulses is a commonly known technique for efficient frequency conversion of cw lasers (see A. Ashkin et al. in "IEEE J. Quantum Electron" vol. QE-2, 1966, 109-123, Eric O. Potma et al. in "Opt. Letters" vol. 28, 2003, p. 19, C. Gohle et al. in "Nature" vol. 436, 2005, p. 234-237, and R. J. Jones et al. in "Phys. Rev. Lett." vol. 94, 2005 p. 193201). With the enhancement cavity, one can enhance the power inside the cavity from a seed mode-locked laser oscillator by a large factor (enhancement factor: typically 10 to 10.000). Among the necessary conditions to realize a large enhancement factor and high average power are the usage of high-damage-threshold, thermally stable intracavity optics of extremely low losses and dispersion control of the cavity.

The first generation of femtosecond enhancement cavities resulted in 28 and 60 fs durations of circulating intracavity pulses of 38 and 480 W average power, respectively (C. Gohle et al. and R. J. Jones et al., cited above). The recent development and power scaling of enhancement cavities with Yb-based fiber amplifiers (see T. Eidam et al. in "Opt. Lett." vol. 35, 2010, p. 94-96) as a seeding source approaches 5 kW level for the cavity with an XUV output coupler in it (see A. Cingöz et al. "Power Scaling of High-Repetition-Rate HHG" in "International Conference on Ultrafast Phenomena", OSA Technical Digest (CD) (Optical Society of America, 2010), paper MD3) and more than 18 kW for the empty cavity (see I. Pupeza, et al. in "Opt. Lett." vol. 12, 2010, p. 2052-2054).

An enhancement cavity can be considered as a passive or an active cavity. In the latter case, the intracavity losses can be compensated by an intracavity active element (WO 2009/092600). Not only passive and active enhancement cavities can be considered for increasing the light power. The opportunity of utilizing high average powers inside the laser oscillator cavities becomes reality with recent progress in high power femtosecond thin disk lasers. Typically, the output coupler transmission T of an oscillator amounts only some percents. It means that power stored inside the oscillator cavity is by factor ~1/T higher than the output power.

At the moment, the intracavity-based high harmonic generation is the most promising way of approaching power-scalable compact and coherent XUV MHz repetition rate sources. However, when XUV radiation is produced inside the cavity, its output coupling immediately becomes a challenging task. XUV light is generated collinearly with the driving fundamental laser beam and can be easily absorbed by even 1 μm-thick condensed matter, for instance by a multilayer structure of the mirror, and exhibits very poor reflectance of the order of ~$10^{-4}$ at normal incidence.

Generally, there is a need for an XUV output coupler (OC) which is designed in consideration of the following criteria:
(a) High XUV output coupling efficiency (ratio of average power of the second radiation component which is coupled out of the cavity (or separated from the first radiation component) to average power of second radiation component (generated inside the cavity)). All XUV light generated inside the cavity should be ideally coupled out.
(b) Broad range of XUV reflectance. In many cases, all generated harmonics of the fundamental driving field (DF) should be collinearly coupled out.
(c) Losses introduced by the OC for DF should be low. These losses include absorption, nonlinear effects, depolarization losses, scattering.
(d) The dispersion introduced by OC, should be small. The contributions to the dispersion are from material (a linear part) and nonlinear effects. Nonlinear effects introducing intensity dependent group delay dispersion (GDD) should be small.
(e) Low thermal lensing: high thermal conductivity and low thermal expansion.
(f) High damage threshold.

Conventional XUV output coupling methods use a Brewster plate, a diffraction grating, a coupling through a hole in a concave cavity mirror, or a non-collinear generation of HHG radiation. It has been found, that the above criteria can be fulfilled by these techniques in a restricted manner only.

The Brewster plate is a plate of a transparent optical quality material placed at the Brewster angle of incidence inside the enhancement cavity between the foci and a concave mirror. In this case, losses of the p-polarized driving light field in the cavity are nearly zero, while a small reflection of XUV occurs at the surface of the plate. One of the main limitations of the Brewster plate is a low XUV out-coupling efficiency (criterion a). Further, the reflection may have a strong wavelength dependency as shown with exemplary reference to the reflection of a sapphire plate in FIG. 10. Thus, the Brewster plate OC has a limited bandwidth (criterion b). Further, the Brewster plate is a compromise between XUV reflectivity and acceptable optical, thermal and nonlinear properties of the Brewster plate material as it is difficult to find a material fulfilling criteria (a) and (f).

The diffraction grating is an XUV grating etched on the top layer of a highly reflective dielectric coating. The structure acts as a relief grating for XUV light and doesn't affect the parameters of the optical beam, thus allowing to avoid any material inside the enhancement cavity and to use only high reflective optics. However, the XUV output coupling efficiency is only comparable to the Brewster plate method achieving e.g. 10% for the 70 nm wavelength (see D. C. Yost et al. in "Opt. Lett." vol. 33, 2008, p. 1099-1101). Furthermore, the maximum intra-cavity power level is limited to e.g. 5 kW and caused by the damage of a dielectric coating (see A. Cingöz, cited above). Thus, this method doesn't meet the above criteria (a), (b) and (f).

For output coupling through a mirror, a small hole is drilled in concave mirror right after the foci of the enhancement cavity. XUV light has less divergence in comparison with DF and can be coupled out through this hole. However, the aperture clips the harmonics of lower orders thus decreasing the XUV bandwidth of out-coupled high harmonics from the long-wavelength side. Furthermore, the hole introduces also losses to the driving light field and decreases the enhancement factor of the cavity.

Finally, the non-collinear HHG utilizes a completely different scheme of HHG. High harmonics are generated in the direction which is non-collinear with the driving beam. The generated XUV light is directed along a bisector of two driving beams. The process may result in conversion efficiencies much lower than that of a "standard" HHG with a single fundamental beam. Moreover, the output coupling efficiency of this method is limited by the cavity design.

Beam splitting of superimposed radiation components is not only a task for coupling higher-harmonic radiation out of enhancement cavities, but also for e.g. XUV output coupling for higher harmonic radiation generated in a laser oscillator cavity or separating the XUV from the fundamental radiation components in single-pass HHG systems. The same task of beam splitting applies for frequency components generated by the fundamental radiation by means of other nonlinear processes than HHG, such as e.g. second harmonic generation (SHG), implemented e.g. in an enhancement cavity or in a single-pass set-up. Moreover, the two frequency components need not be correlated by a nonlinear process, but can stem from uncorrelated radiation sources.

Separating XUV radiation from IR radiation is also mentioned by M. De Grazia et al. in "Proc. of SPIE", vol. 6586, 2007, p. 658601-658610. A plate carrying one antireflective coating on one surface thereof is arranged with an angle of incidence of possibly about 60° for reflecting the XUV radiation while transmitting the IR radiation. As a main disadvantage, this conventional technique was restricted to relatively low harmonics (up to 21th harmonic). For higher harmonics, i.e. for lower wavelengths, which occur in particular in enhancement cavities, the efficiency of the conventional reflecting plate is too low. Furthermore, the conventional reflecting plate could not be used in an enhancement cavity as the IR radiation component is split by the plate to different directions. This would result in an unacceptable lost in circulating IR intensity.

Outcoupling EUV light from a cavity by using an intracavity diffraction grating has been mentioned by A. Cingöz et al. in "Internat. Conference on ultrafast phenomena" (1 Jan. 2010). With this technique, the diffraction grating is formed at one of the cavity mirrors. The diffraction grating has an essential disadvantage in terms of spatially dispersing EUV components.

Further beam splitting techniques are known, which use dichroic plates (see e.g. U.S. Pat. No. 6,147,806 A, US 2010/007860 A1). However, these techniques cannot be applied if the short wavelength component has a wavelength in a range of e.g. XUV radiation, as the wavelength separation is done within the plate volume, where the XUV radiation would be lost due to absorption.

Furthermore, the task of combining two spatially separated beams with different frequency components is closely related to their separation and can typically be solved by operating a beam splitting device in the opposite propagation direction. Conventional techniques use dichroic mirrors for combining beams with different wavelengths. However, the application of dichroic mirrors is restricted if one of the beams has a wavelength in the XUV range as this beam would be absorbed by the dichroic mirror.

OBJECTIVE OF THE INVENTION

The objective of the invention is to provide an improved method of spatially relaying radiation components with different wavelengths, wherein the beam relaying method is to be capable of avoiding disadvantages of conventional techniques. In particular, a beam relaying method is to be capable of output coupling higher harmonic radiation e.g. from an enhancement cavity, whereas criteria for operating the enhancement cavity can be optimized. Furthermore, the objective of the invention is to provide an improved optical relaying device being capable of wavelength-selective separation or combination of radiation components while avoiding disadvantages of conventional techniques. Furthermore, the objective of the invention is to provide an improved method of output coupling second or higher harmonic radiation from an optical resonator, like an enhancement cavity or a laser resonator, and/or an improved resonator device, like an enhancement cavity or a laser resonator provided with an optical relaying device.

These objectives are solved by methods and/or devices comprising the features of the invention.

SUMMARY OF THE INVENTION

According to a first general aspect of the invention, a method of spatially relaying a first radiation component having a first wavelength and a second radiation component having a second wavelength different from the first radiation component is provided, wherein an optical relaying device with a transparent plate having anti-reflection coatings on both side surfaces thereof is used. According to the invention, the first radiation component is transmitted across the optical relaying device with predetermined incident and emergent angles, resp. The optical relaying device is arranged in a first beam path of the first radiation component such that it travels through the plate forming the incident and emergent angles. Furthermore, according to the invention, the anti-reflection coatings are effective for the first radiation component at the incident and emergent angles, resp. Accordingly, the reflection of the optical relaying device is reduced by the anti-reflection coatings. Reflections exclusively of the first radiation component are suppressed at the optical relaying device, while, according to the invention, the second radiation component is reflected at the optical relaying device with a predetermined reflection angle. The optical relaying device is arranged in a second beam path of the second radiation component such that it hits the optical relaying device with the reflection angle. The reflection angle is equal to at least one of said incident and emergent angles of the first radiation component. Thus, if both the first and second radiation components travel along a common beam path towards the optical relaying device, the second radiation component is reflected while the first radiation component is transmitted through the transparent plate. Alternatively, if the first and second radiation components travel along different beam paths towards the optical relaying device, they can be adjusted such that after transmission and reflection, the transmitted first radiation component and the reflected second radiation component travel along a common beam path. Thus, depending on the travel directions, the first and second radiation components are split from each other toward different directions or combined into a common beam path using the optical relaying device.

According to a second general aspect of the invention, an optical relaying device is provided, which is adapted for spatially splitting or combining radiation components, preferably with a method according to the above first aspect of the invention. The optical relaying device comprises a transparent plate, which is capable of transmitting a first radiation component having a first wavelength with predetermined incident and emergent angles, resp., and which is capable of reflecting a second radiation component with a predetermined reflection angle being equal to at least one of said incident and emergent angles. The wavelengths of the first and second radiation components differ from each other. According to the invention, a first anti-reflection coating is formed on a first side of the transparent plate, and a second anti-reflection coating is formed on a second, opposite side of the transparent plate. The first and second anti-reflection coatings are designed such that the first radiation component is transmitted through the optical relaying device without or with negligible reflections at at least one of the incident and emergent angles.

Advantageously, the invention provides an extension of the conventional Brewster plate concept e.g. as an XUV output coupler inside enhancement cavities where high harmonics of the fundamental radiation (driving field circulating in an enhancement cavity) are generated. With the use of the anti-reflection coatings, the restriction to use the Brewster angle can be avoided. The optical relaying device can be arranged in a beam path with an angle above the Brewster angle, where the reflection of the second radiation component is increased and has a reduced wavelength dependency. Thus, the optical relaying device is also called gracing incidence coated plate. With the preferred application as an output coupler in an optical resonator, the proposed optical relaying device serves as a low-loss plate for the circulating fundamental light inside the resonator cavity and as a highly efficient, extremely broadband output coupler e.g. for XUV. Potentially, the short-wavelength reflectivity of the optical relaying device can be extended to a keV range.

The following further advantages are obtained with the invention.

1. An ultrabroadband optical relaying device or output coupler (0° C.) is provided that can cover all the XUV-VUV-UV-VISIR-MIR-FIR range and more. In particular, the first radiation component has a wavelength selected in a range of XUV to FIR wavelengths. For preferred optical applications, the first radiation component has a wavelength in a range from 800 nm to 1300 nm. The first and second radiation components have different wavelengths. The minimum wavelength difference is defined by a bandwidth of anti-reflection coating. The wavelength of the second radiation component is outside the bandwidth of the first radiation component. The second radiation component has a wavelength selected in a range of keV-X-ray to FIR wavelengths, in particular from 1 nm to 150 nm. Presently, preferred applications are with wavelengths equal or below 40 nm, e.g. the 13 nm range (an existing lithography) or the so-called water-window range (around 4 nm).

2. Compared with conventional techniques, the optical relaying device has an increased efficiency (can be more than 50% through all the XUV-VUV-UV-VIS-IR-MIR-FIR range).

3. Compared with conventional techniques, the optical relaying device has reduced losses for the first radiation component, e.g. a fundamental field in an optical resonator (theoretically can be as low as 0.001% or even 0.0001%, the realised loss is 0.1%).

4. The optical relaying device can provide a dispersion control in an optical resonator, this is particularly important for short intracavity circulating pulses.

5. The optical relaying device can operate for any certain polarisation or even used as a polarisation filter.

6. The optical relaying device can be used inside a passive or active enhancement cavity or inside the laser oscillator cavity), or outside the cavity.

7. The optical relaying device can be used as a dichroic beamsplitter, as a beam combiner (i.e. reverse to beamsplitter) or as a filter. In the latter case, the residual fundamental can be further suppressed by using a set of the optical relaying devices outside the cavity.

8. Compared with conventional techniques, the optical relaying device has a high-damage threshold (higher than that for the intracavity multilayer mirrors).

9. The optical relaying device can be used as an intracavity spatial filter for filtering the fundamental mode.

10. The optical relaying device can be of low nonlinearity to avoid nonlinear effects based on $n_2$ or even of high nonlinearity for exploiting a) $n_2$ (Kerr lens effect for mode-locking or spectral broadening) or b) $\chi^2$ or $\chi^3$ for any low-efficient nonlinear process as DFG, THG, Raman etc.

11. The optical relaying device can be of very high surface quality giving thus a high-quality beam containing all new spectral components.

Each of the first and second radiation components may comprise continuous wave (cw) or pulsed radiation having a certain wavelength. Despite of the real spectral width of the radiation, in particular in the case of pulsed radiation, the radiation component wavelength refers to a mean or centre wavelength of the electromagnetic field. In the present specification, each of the incident, emergent and reflection angles is defined as an angle measured relative to a transparent plate surface normal of the optical relaying device at the location of incidence/exit. The transparent plate of the optical relaying device is made of an integral or composite dielectric or semiconductor material which is transparent (in particular clear and free of absorptions) at the wavelength of the first radiation component. Furthermore, the transparent plate material is characterized by a specific Brewster angle with respect to the wavelength of the first radiation component.

According to a preferred embodiment of the invention, the transparent plate of the optical relaying device is arranged such that incident (or emergent) angle of the first radiation component and the reflection angle of the second radiation component is larger than the Brewster angle of the transparent plate material, because of the high reflection of the second radiation component. Preferably, a grazing incidence is implemented. Particularly preferred, the incident (or emergent, exit) and reflection angle is at least 55°, e.g. at least 65°, in particular at least 70°. Furthermore, the incident (or emergent, exit) and reflection angle can be nearly 90°, preferably, it is at most 89.5°, in particular at most 85°.

With a preferred application of the invention, the first and second radiation components are split from a common primary beam. Before splitting, the first and second radiation components are collinearly superimposed and directed along a common primary beam path onto the optical relaying device. Accordingly, both of the first radiation component and second radiation component have the same incident angle relative to the transparent plate. On the anti-reflection coating of the transparent plate, the second radiation component is reflected with a reflection angle equal to the incident angle, while the first radiation component is transmitted through the transparent plate. Thus, after splitting, the first and second radiation components travel along different spatial directions. With the splitting application of the invention, the first radiation component preferably is a fundamental radiation resonantly circulating in a resonator cavity, e.g. in an active or passive enhancement cavity and/or a laser resonator, while the second radiation component is a secondary radiation generated in the resonator cavity by an interaction of the fundamental radiation with a target medium, like e.g. a gas jet of a noble gas.

With an alternative application of the invention, the first and second radiation components are combined into a common secondary beam. The first radiation component is directed onto the optical relaying device along a first primary beam path, while the second radiation component is directed onto the optical relaying device along a different, second primary beam path. Both primary beam paths are adjusted such that, after transmission and reflection, the reflection angle of the second radiation component is equal to the emergent angle of the first radiation component and both first and second radiation components are superimposed into a common secondary beam path.

Advantageously, there are no particular requirements with regard to the shape of the transparent plate. The transparent plate can be designed in dependency on the conditions of application of the invention. As a preferred example, the transparent plate is a plane-parallel plate, so that the incident and emergent angles of the first radiation component are equal. Advantageously, this results embodiment introduces a displacement of the first radiation component only (depending on the plate thickness), while the orientation of the first radiation component e.g. within a resonator is kept. Preferably, the thickness of the transparent plate is at least 10 µm, in particular at least 200 µm. Furthermore, the thickness of the transparent plate is preferably at most 6 mm, in particular at most 1 mm. As an alternative preferred example, the transparent plate is a wedged plate, so that the incident and emergent angles of the first radiation component differ from each other. With this embodiment, the optical relaying device can be used for deflecting the first radiation component e.g. within the optical resonator. Additionally or alternatively, the transparent plate may have at least one plane and/or at least one curved plate surface, so that the optical relaying device can fulfil beam forming or imaging functions.

As a further advantage, there are no particular requirements with regard to the material of the transparent plate, which can be made of each material transparent for the first radiation component. According to preferred applications with an optical first radiation component, the transparent plate can be made of fused silica, crystalline quartz, $CaF_2$, or synthetic quartz glass. Furthermore, the material of the transparent plate can have an optical nonlinearity, such that additional spectral components can be generated by an interaction of the first radiation component with the transparent plate in or outside a cavity. To this end, the transparent plate is made of e.g. lithium triborate LBO, monopotassium phosphate KDP, β-barium borate BBO, or periodically poled lithium niobate PPLN.

The anti-reflection coatings provide suppressed reflectivity for the first radiation component. To this end, the anti-reflection coatings preferably have multilayer structures, made of e.g. $SiO_2$ and $Nb_2O_5$ layers, $SiO_2$ and $Ta_2O_5$, $SiO_2$ and $Al_2O_3$.

The optical relaying device can fulfil further functions, if according to another embodiment the anti-reflection coatings are designed such that they provide a polarization and/or a wavelength filter. In particular, the anti-reflection coatings can be adapted for polarizing of the first radiation component. Polarization is obtained by adjusting the multilayer structure of the anti-reflection coating so that different polarisations at large angles of incidence have different reflectivities. The anti-reflection coating can be designed either for p or s polarization and simultaneously can exhibit selective losses for s and p polarizations. Furthermore, the anti-reflection coatings can introduce spectral selectivity for the first radiation component (spectral filter).

Additionally or alternatively, the anti-reflection coatings are designed such that they introduce a predetermined dispersion into the beam path of the first radiation component. Thus, the optical relaying device can be used for pulse shaping of the first radiation component in the resonator. In particular, dispersion can be introduced which is adjusted for maintaining femtosecond intracavity pulses circulating in an enhancement cavity.

If the transparent plate of the optical relaying device has a high nonlinearity and simultaneously provides target medium for generating new spectral components, the anti-reflection coatings of the transparent plate preferably are designed as follows. The first anti-reflection coating preferably is transparent for the first and second radiation component, while the second anti-reflection coating preferably is transparent for the first radiation component being either reflective or transparent for the new spectral components.

According to a third general aspect of the invention, a method of out-coupling harmonic radiation from an enhancement cavity is provided, wherein the radiation relaying method of the above first aspect is used. According to the invention, the second radiation component (second or higher harmonic radiation) is generated in the enhancement cavity by an interaction of the first radiation component (fundamental radiation) with a target medium. The second or higher harmonic radiation is split from the fundamental radiation with the inventive relaying method. The optical relaying device according to the above second aspect of the invention is arranged in the enhancement cavity such that the fundamental radiation is transmitted essentially without changes or with an intentional predetermined polarization, spectral composition and/or spatial orientation. Preferably, the enhancement cavity includes a cavity section with two curved mirrors which define a focus position, where the target medium is arranged for second or higher harmonic generation. With this embodiment, the optical relaying device is preferably arranged in the cavity section between one of the two curved mirrors and the focus position. As an advantage, this allows the most efficient output coupling of the second radiation component.

Alternatively, the optical relaying device can be arranged outside the cavity section with the two curved mirrors and the focus position.

According to a third general aspect of the invention, a method of conducting a pump-probe measurement of a sample is provided, wherein the radiation relaying method of the above first aspect is used. According to the invention, the first radiation component (fundamental radiation) is created by a laser, and a pump beam is split from the fundamental radiation towards a first primary beam path. A probe beam is created by generating second or higher harmonic radiation from the fundamental radiation, wherein the probe beam travels along a second primary beam path. Both first and second primary beam paths are superimposed into a common secondary beam path with the inventive relaying method. A sample to be investigated by the pump-probe measurement is arranged the in the common secondary beam path, the sample is subjected to the pump and probe beams.

According to a fourth general aspect of the invention, a resonator device, in particular an enhancement cavity device or a laser resonator is provided, which comprises a plurality of cavity mirrors spanning a cavity beam path and including two curved cavity mirrors which are adapted for focussing a fundamental radiation component along the cavity beam path at a focus position of a target medium in the cavity beam path. The resonator device has a passive or an active (i.e. containing an active medium) cavity or laser cavity. According to the invention, the inventive optical relaying device is arranged in the cavity such that the transparent plate is crossed by the cavity beam path. Preferably, the curved cavity mirrors are arranged for an asymmetric focusing. Thus, the focus is spaced with different path lengths from each of the curved cavity mirrors, so that sufficient space for arranging the optical relaying device is provided.

BRIEF DESCRIPTION OF THE DRAWINGS

Further details and advantages of the invention are described in the following with reference to the attached drawings, which show in.

PREFERRED EMBODIMENTS OF THE INVENTION

Embodiments of the invention are described in the following with particular reference to the design of the optical relaying device and the application thereof, in particular for output coupling of higher harmonic radiation from an enhancement cavity. Details of the cavity design or operation, in particular the HHG process is not described as it is known as such from prior art. It is emphasized that the invention is not restricted to the enhancement cavity application but rather can be implemented in an analogue manner e.g. in a XUV, UV, or VIS output coupling device for second or higher harmonics generated inside a high-power laser oscillator cavity or for separating the XUV, UV, or VIS from the fundamental radiation in single-pass systems. Generally, the enhancement cavity approach can be applied not only for generating XUV but also for any low-efficient nonlinear process creating new spectral components that does not affect the fundamental intracavity light. Therefore, this approach can be extended towards VUV-UV-VIS-IR-MIR-FIR and beyond.

Figure 1:
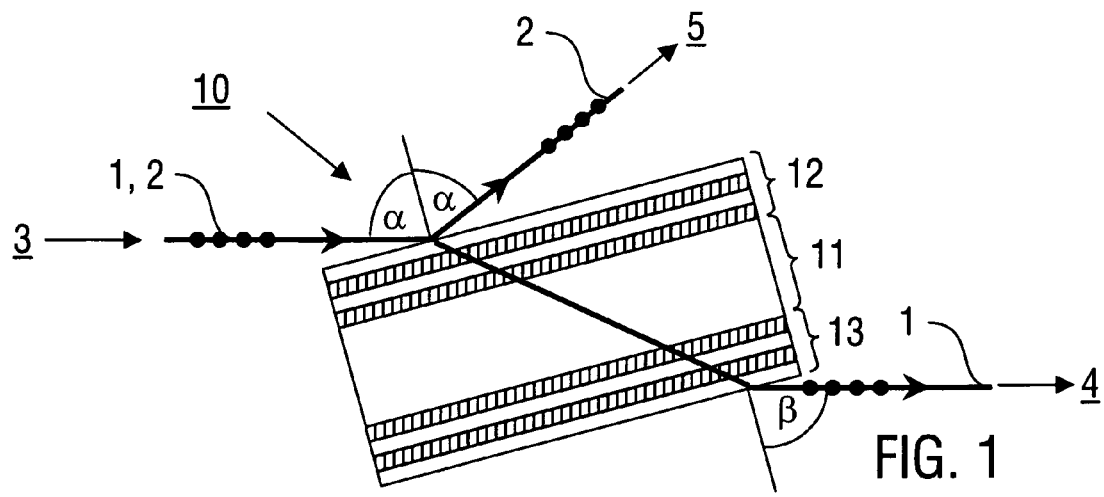
FIG. 1: a sectional view of an optical relaying device according to a preferred embodiment of the invention arranged for splitting first and second radiations components.

According to the invention, the optical relaying device can be used as a radiation splitting device or as a beam paths combining device. In FIG. 1, exemplary reference is made to the splitting function of the optical relaying device. It is emphasized that the beam paths combining function can be realized in an equal manner simply by reversing the traveling directions of the radiation beams (see FIGS. 6, 7).

Features of an optical relaying device 10 and spatial splitting of a first radiation component 1 and a second radiation component 2 travelling along a common primary radiation beam path 3 are described in the following with reference to FIG. 1. The optical relaying device 10 (shown with a schematic cross-sectional view, not to scale) comprises a transparent plate 11 having anti-reflection coatings 12, 13 on both side surfaces thereof. The transparent plate 11 comprises e.g. a fused silica plate having a thickness of 50 μm and diameter of 20 mm. In particular with the enhancement cavity embodiment (see FIG. 8), the transparent plate 11 comprises a substrate material with the best available optical quality, thermal properties and low nonlinearities in order to push the limits of the achievable intra-cavity circulating power. Examples, in particular for the enhancement cavity embodiment, are fused silica, crystalline quartz, $CaF_2$ and Suprasil 3002 (trade name).

The anti-reflection coatings 12, 13 each comprise a stack of e.g. layers having alternately lower and higher refractive indices. Typically, fused silica ($SiO_2$) is used as a low refractive index material in the multilayer anti-reflection coatings 12, 13. This material is well studied in both XUV and near infra-red wavelength ranges. The optical constants of different modifications of fused silica have been measured and tabulated. In particular, fused silica can be chosen as the material of a top layer of the anti-reflection coating 12 and/or 13 in the optical relaying device 10. Furthermore, $Nb_2O_5$ is used as a high refractive index material. In other words, the structure of the anti-reflection coatings 12, 13 comprises alternating $SiO_2$ and $Nb_2O_5$ layers. These materials have largest difference of low and high refractive indices, therefore they were chosen as an optimal choice to achieve low residual reflectivity at the oblique incidence. The coatings have been designed with a commercial software package "Optilayer" (www.optilayer.com), e.g. for 75° angle of incidence at the central wavelength 1030 nm. As an advantageous variant, the robust design of an anti-reflection coating consisting of only 3 pairs of $SiO_2$ and $Nb_2O_5$ can been chosen in order to reduce the manufacturing time and corresponding accumulated errors. However, more complex multilayer structures with broader bandwidth and increased angle of incidence are possible.

The implementation of the invention is not restricted to the use of $SiO_2$ and $Nb_2O_5$. Other materials, like e.g. $Ta_2O_5$ or $Al_2O_3$ can be used as further examples. With $Ta_2O_5$ (optical constants of this material are known in spectral range from 150 nm to 8000 nm) the design shown in FIG. 5, has >50% reflectivity in the ranges 135 nm to 140 nm, 142 nm to 152 nm, 155 nm to 175 nm, 185 nm to 215 nm, 240 nm to 290 nm, 300 nm to 315 nm, 380 nm to 480 nm, 500 nm to 600 nm, 1200 nm to 1700 nm, 2000 nm to 3300 nm, and smooth reflectivity >30% in the whole range 3500 nm to 8000 nm. By varying designs and materials, one can expect other broadband smooth ranges of high reflectivity.

Generally, the material, order and thicknesses of the anti-reflection coating sub-layers are calculated and optimized using commercial software in dependency on the conditions of a particular application of the invention, in particular in dependency on the wavelength of the first radiation component, optional further functions of the optical relaying device 10, and the incident and emergent angles. The anti-reflection coatings are made with conventional techniques as they are known from the manufacturing of dielectric mirrors, e.g. by magnetron sputtering.

The idea of an efficient and broadband XUV output coupler is similar to the Brewster plate output coupling method: the plate provides lowest possible losses for the first radiation component and significant reflection for the second radiation component (XUV). In contrast to the Brewster plate, the inventors proposed to coat both sides of the transparent plate 11 with the anti-reflection (AR) coatings for the large angle of incidence of the first radiation component. At the large angle of incidence (e.g. >75°), XUV light has drastically increased reflectivity (see FIG. 2) as it follows from the Fresnel equations. This effect can be used to enhance the XUV reflectivity by fabricating a low-loss AR coating for the first radiation component (e.g. infrared radiation) at both sides of the plate 11 as it shown in FIG. 1. Due to the anti-reflection effect of the anti-reflection coatings 12 and 13, the first radiation component 1 is transmitted through the transparent plate 11 towards a first secondary beam path 4, while the second radiation component 2 (XUV radiation) is reflected towards a second secondary beam path 5.

Figure 2:
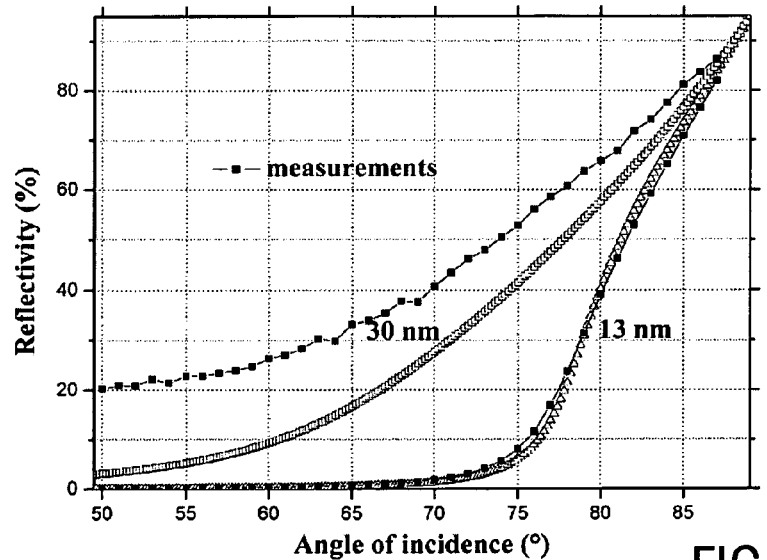
FIGS. 2 to 5: graphical representations of reflectivity and transmission properties of an optical relaying device and parts thereof.

The angle reflectivity of $SiO_2$ for s-polarized 13 nm and 30 nm XUV radiation is illustrated in FIG. 2. Measured reflectivity at 13 nm wavelength is in excellent agreement with calculated reflectivity based on the optical constants known from literature. Measured reflectivity at 30 nm is higher than the calculated one what can be explained by difference in chemical composition of tabulated fused silica and fused silica used in the practical experiment. FIG. 2 shows that the reflectivity is increased with increasing reflection angle. As the reflection angle of the optical relaying device 10 can be increased compared with the conventional Brewster plate technique, the efficiency of output coupling can be increased.

Figure 3:
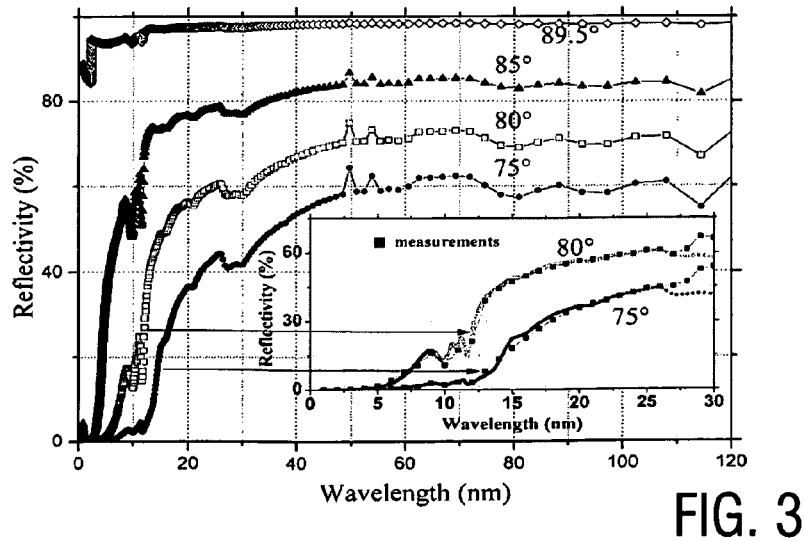
Figure 10:
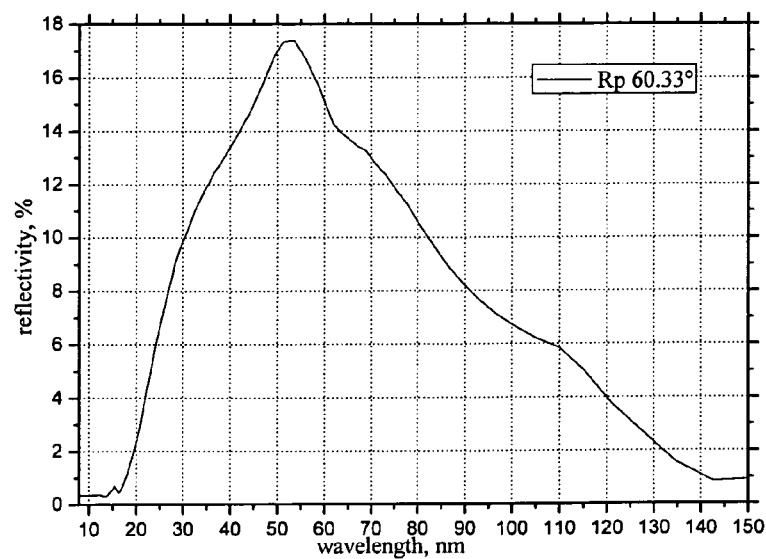
FIG. 10: a graphical representation of an XUV reflectivity of a conventional sapphire Brewster plate output coupler.

In FIG. 3, measured and simulated XUV reflectivity spectra are shown for the different angles of incidence. The inset shows a comparison between measured XUV reflectivity and calculated one at 75°, 80° angles of incidence. Contrary to the spectra of FIG. 10, the invention provides a broadband reflectivity. At the oblique incidence larger than 75° and s-polarized light, the XUV output coupling has reasonable reflectivity (~15%) even at the wavelength 15 nm. For the preferred maximal angle 89.5°, the reflectivity at the wavelength 1 nm is expected to be as high as 80%. The expected reflectivity values at such short wavelengths can be reduced because of the surface irregularities which are close to the size of the XUV wavelength. For instance, the lowest roughness of BK7 substrate from manufacturer Layertec GmbH, Germany, is equal to 0.5 nm and due to the coating procedure can be substantially increased at the upper surface. Surface imperfections causes scattering of XUV light and result in reduced XUV reflectivity.

Figure 4:
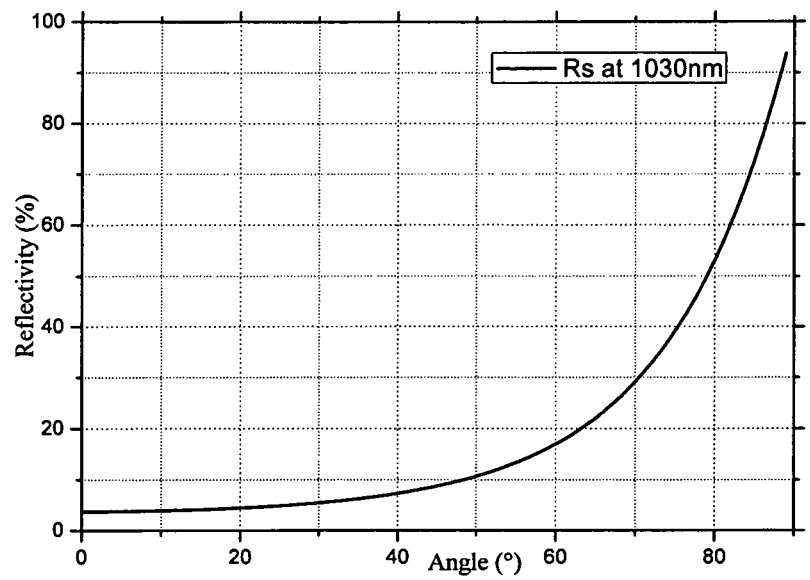

FIG. 4 illustrates the reflectivity of the s-polarized light from fused silica at 1030 nm at different angles of incidence. From the principle of operation, any multilayer coating has an angle dependence of the reflection. Conventionally, anti-reflection coatings are designed for the normal incidence and suppress only some percents of reflectivity (in case of fused silica the value is 4%) at the material-air interface. It is one of the main and surprising results of the present invention that the anti-reflection coatings can be designed such that a suppression of 50% of the incident light can be obtained at the angles of incidence even around 75° to 80° in order to achieve a low loss antireflective coating. The second important result of the present invention is the finding that a low sensitivity of the residual reflection of the first radiation component to the incidence angle variations (the accepted angle of incidence) is provided. On the other hand, the transparent plate 11 of the optical relaying device 10 can be even used as a spatial filter. The anti-reflection coatings can be designed such that angle-dependent losses occur and higher order cavity modes which exhibit higher divergence can be suppressed.

Figure 5:
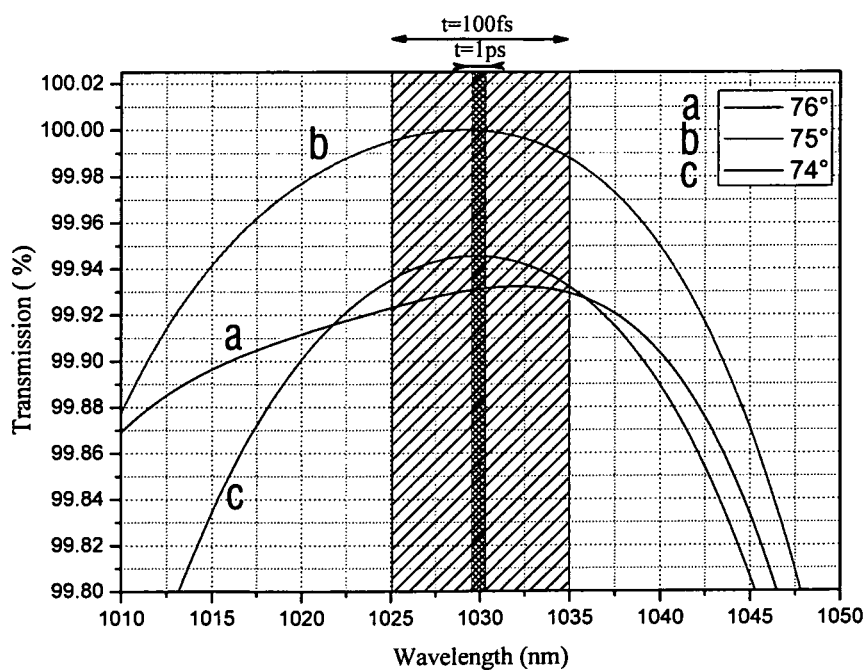

The simulated spectral transmission of the anti-reflection coatings 12, 13 is shown in FIG. 5 for different angles of incidence. The anti-reflection coating was optimized for 75°.

The transmission is shown for one side of the two-side coated substrate plate. The shadowed areas correspond to the spectral width of 1 ps and 100 fs pulses and show the general tendency of the reduced average reflection for shorter pulses. One can see that the losses for the bandwidth-limited $sech^2$ shaped 100-fs pulse corresponding to the 11 nm spectrum are below 0.2%. The simulated spectral transmission results have been confirmed in test experiments. Furthermore, in order to confirm the negligible sensitivity of the anti-reflection coating to the beam divergence, the beam was focused by a lens and residual reflections were measured. The reflected power stayed the same as in the previous test experiment, thus demonstrating insensitivity of the coating to the beam divergence.

In comparison to the conventional XUV output couplers, the invention has the following further advantages. High XUV reflectivity is obtained due to the large angle of incidence and s-polarized light (see FIG. 2). At the angle of incidence equal to 80°, the reflectivity reaches even 70% at 50 nm wavelength and 16% at 9 nm. An ultra-broad XUV spectrum range is obtained (see FIG. 3). At 80° angle of incidence, the spectral range from 13 nm to at least 120 nm is covered with the efficiency of more than 40%. For comparison, the Brewster plate method shows 10% efficiency at the boarders of the range 30 to 80 nm (see FIG. 10). The XUV reflection spectrum of optical relaying device 10 can be even more extended, into VUV and beyond. Depending on the parameters of the materials used, an anti-reflection design of optical relaying device 10 can be made e.g. for the range 150 nm to 400 nm. A high damage threshold is obtained. The anti-reflection coatings 12, 13 have higher damage threshold in comparison to a high reflectance coating containing more layers, and approaches the damage threshold of bulk material. The grazing angle of incidence increases the effective interaction area at the optical relaying device surface and as a consequence reduces the peak intensity at the sample leading to higher damage threshold.

Furthermore, the anti-reflection coatings 12, 13 can be used for introducing a dispersion control. Nonlinear phase shift of the circulating pulse in a optical relaying device 10 as well as material dispersion (input coupler of an enhancement cavity) can be compensated by a properly designed AR coating.

A further advantage of the optical relaying device 10 results from the polarization sensitivity of the anti-reflection coating 12, 13. Theoretically, the anti-reflection coating has a residual reflection of around 40% for the p-polarized first radiation component and has no reflection for the s-polarized light thus making the optical relaying device 10 a polarizer. Polarization sensitivity is a used for the Hänsch-Couillaud method of locking an enhancement cavity to the seeding oscillator (see T. Hänsch et al. in "Opt. Comm." vol. 35, 1980, p. 441).

Figure 6:
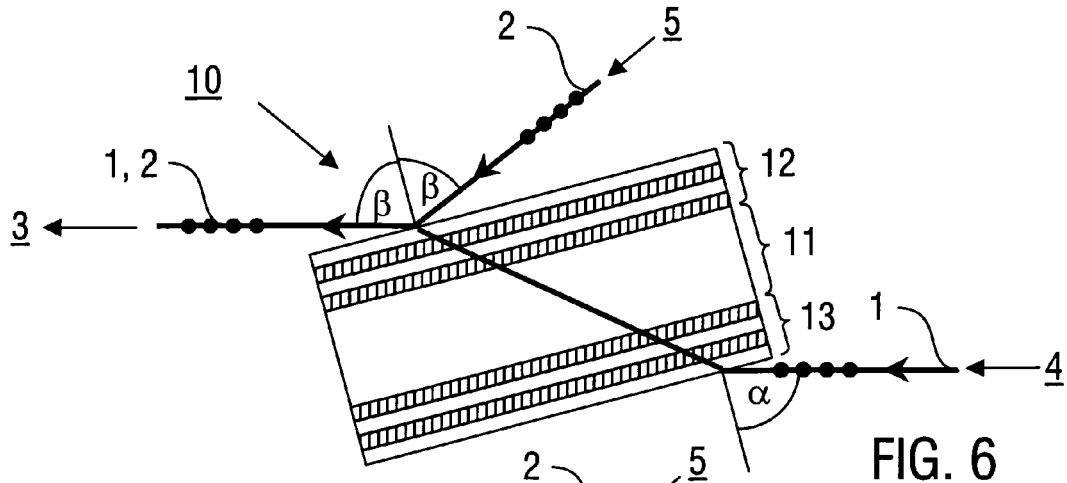
FIGS. 6 and 7: sectional views of optical relaying devices according to further preferred embodiments of the invention arranged for combining first and second radiations components.

Another embodiment of the invention includes combining the first radiation component 1 travelling along a first primary beam path 4 and the second radiation component 2 travelling along a second primary beam path 5 as shown in FIG. 6. In this case, the optical relaying device 10 has the same design as in the case of splitting radiation components (FIG. 1). The first radiation component 1 is directed onto a first anti-reflection coating 13 of the optical relaying device 10 with an incident angle α and transmitted trough the optical relaying device 10 such that an emergent angle β is formed at the second anti-reflection coating 12. The second radiation component 2 is directed with an incident angle β equal to the emergent angle β onto the second anti-reflection coating 12 at the exit location of the first radiation component 1. Thus, both first radiation component 1 and second radiation component 2 are superimposed into the common secondary beam path 3.

Figure 7:
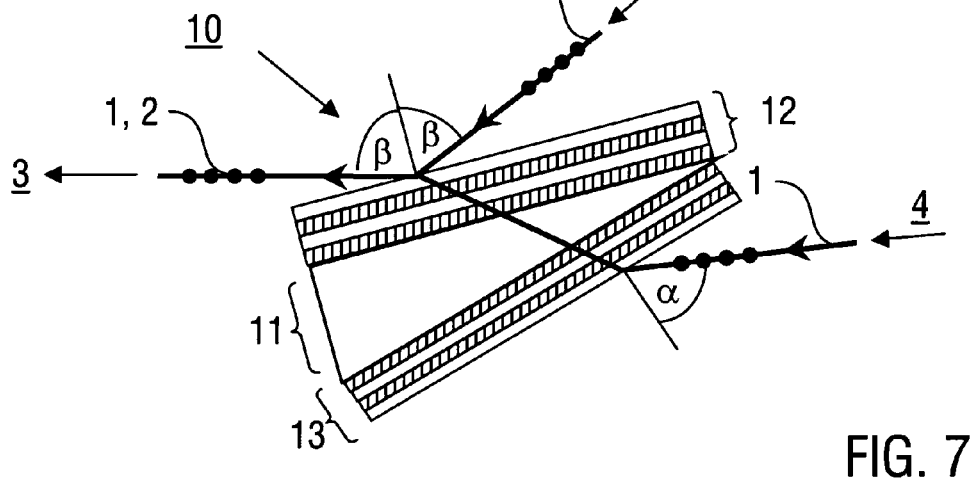

While FIGS. 1 and 6 illustrate an optical relaying device 10 with a plan-parallel plate 11, other plate shapes are possible. As an example, FIG. 7 shows a wedged plate 11 carrying on both sides anti-reflection coatings 12, 13, resp. The wedge angle of the wedged plate 11 is e.g. 2°. In this case, the incident angle α and the emergent angle β of the first radiation component 1 differ from each other. Again, for combining radiation components, the second radiation component 2 is directed with an incident angle equal to the emergent angle β of the first radiation component 1 onto the second anti-reflection coating 12 at the exit location of the first radiation component 1.

Figure 8:
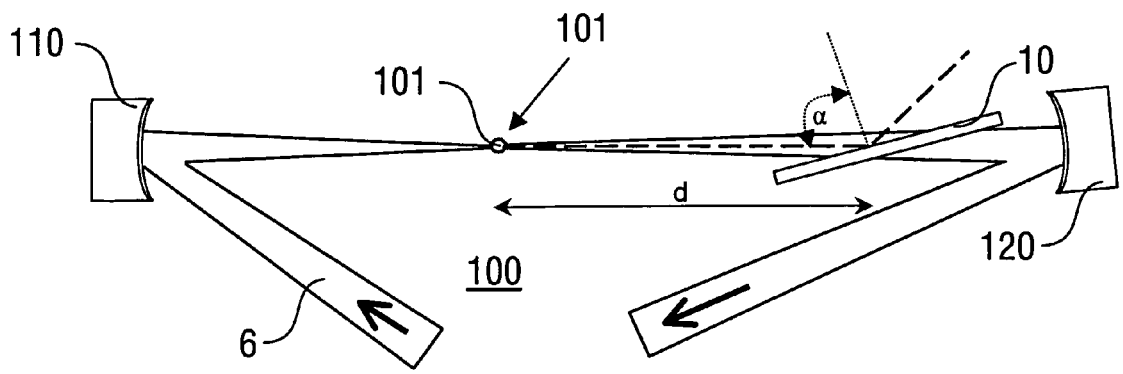
FIG. 8: an embodiment of an inventive enhancement cavity provided with the optical relaying device of FIG. 1 and adapted for implementing the inventive relaying method.

FIG. 8 illustrates the implementation of the optical relaying device 10 as an output coupler inside an enhancement cavity 100. Basically, the enhancement cavity 100 comprises a plurality of cavity mirrors spanning a cavity beam path 6. FIG. 8 shows only two of the cavity mirrors, namely two curved cavity mirrors 110, 120 which focus a first radiation component 1 (fundamental radiation) along the cavity beam path 6 at a focus 111. The remaining cavity mirrors are arranged as it is known from conventional cavities, e.g. in a folded or circular configuration. A target medium 101, e.g. a Xe gas jet is arranged in the focus 111 for an irradiation with the first radiation component 1. Due to the interaction of the first radiation component 1 with the target medium, XUV radiation is generated which travels as the second radiation component 2 along the cavity beam path 6. The generated XUV radiation is polarized parallel to the linearly polarized first radiation component 1, (e.g. s-polarized). The optical relaying device 10 is arranged in the cavity beam path 6 such that the first and second radiation components 1, 2 hit the optical relaying device 10 with an incident angle α, e.g. 75°. The fundamental radiation is transmitted trough the optical relaying device 10 while the XUV radiation is deflected out of the enhancement cavity 100, e.g. to an experimental set-up. As an advantage of the polarization of the XUV radiation, the delivering of the out-coupled XUV beam to the experiment involves further XUV optics which in general has better reflectivity for s-polarization.

The optical relaying device 10 is placed e.g. between the foci and one of the concave mirrors 110, 120 in standard symmetric or asymmetric cavity configuration. Asymmetric cavity configuration (for instance, radius of curvature of the first concave mirror is 100 mm and of the second one is 200 mm) allows one to extend the distance d between the foci and the concave mirror in order to be able to place a optical relaying device 10 closer to the mirror thus increasing the spot size on it and decreasing the damage probability. The grazing incidence plate 10 placed between two focusing mirrors 110, 120 compensates astigmatism induced by the not normal angle of incidence at focusing mirrors. For very thin plates (e.g. thickness ≤100 μm) this effect is rather negligible. Advantageously, the optical relaying device 10 can be of large size allowing thus to position it alternatively in any place inside the cavity at almost any angle (in the focus, near the focus, near the cavity mirrors).

Due to the divergence of the first radiation component beam 1 falling onto the optical relaying device 10 (see FIG. 8), the incident angles are different for the central part of the first radiation component 1 and its periphery. In the case of a typical cavity, this difference can be as high as 1° (ROC of mirrors 110, 120 are 150 mm). This divergence is uncritical due to the low angle dependency of residual reflections of the first radiation component 1 or even intentionally used for adjusting the transversal mode of the first radiation component 1 inside the cavity.

Advantageously, the optical relaying device 10 couples out the collinearly co-propagating fundamental and any created new-frequency radiation. For the generated XUV harmonics, it can lead to the generation of attosecond pulses. It can provide a simple self-aligned (i.e. self-overlapped) radiation (both fundamental and of new frequencies) for a pump-probe experiment (similar to that of FIG. 9, below). Furthermore, the optical relaying device can reflect all the radiation circulating or generated in the cavity including the fundamental radiation. By varying the parameters of the anti-reflection coatings of the optical relaying device 10, one can control the amount of fundamental radiation light coupled out of the cavity.

Furthermore, the optical relaying device 10 can be used not only inside the passive enhancement cavity 100 but also inside an active enhancement cavity, inside a laser oscillator cavity or even outside. The optical relaying device 10 can be designed for any certain polarization state. Owing to its polarization properties, the optical relaying device 10 can be used not only as a dichroic beam splitter but also as a filter or a beam combiner as shown in the following.

Figure 9:
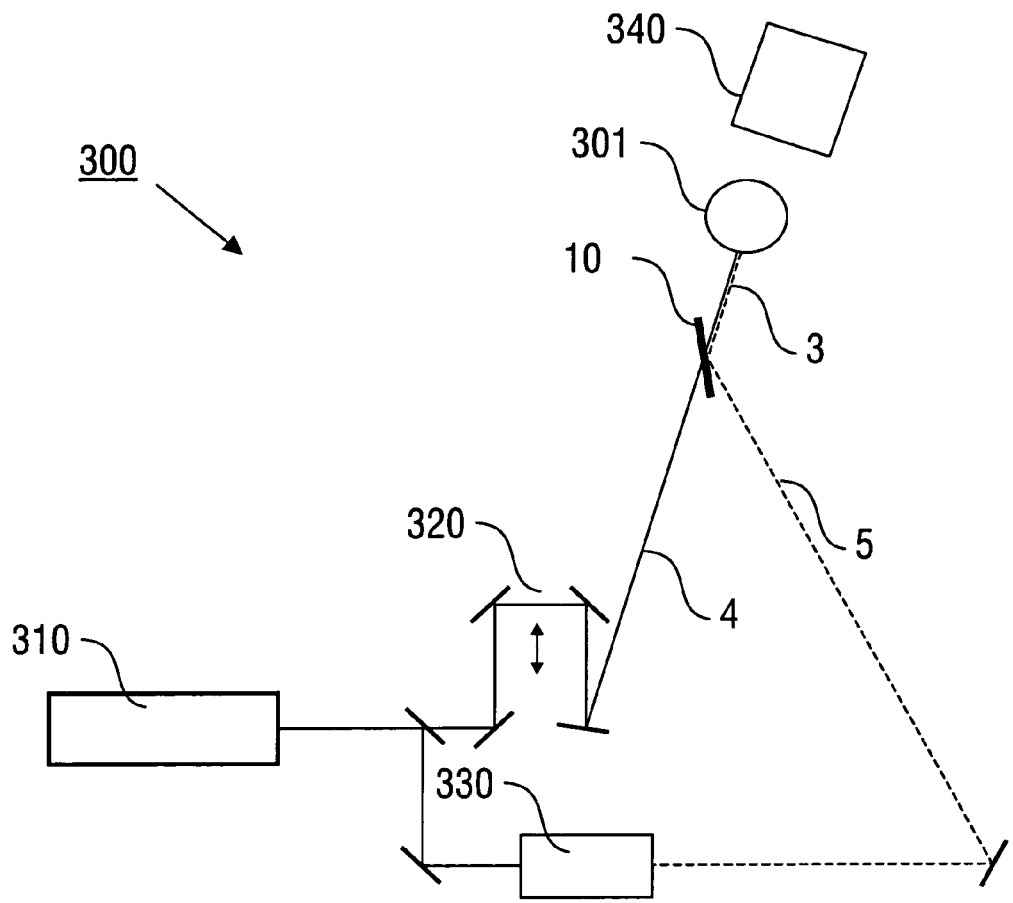
FIG. 9: an embodiment of a pump-probe-measurement setup provided with the optical relaying device of FIG. 6.

FIG. 9 schematically illustrates an application of the beam paths combining embodiment of the invention with a pump-probe measurement setup 300. Fundamental radiation having an optical wavelength is created with a pulse laser 310. The fundamental radiation provides a pump beam travelling via a time delay section 320 along a first primary beam path 4 to the optical relaying device 10. Another portion of the fundamental radiation is input in a device 330 for generating second or higher radiation, e.g. XUV radiation, creating a probe beam with a wavelength shorter than the wavelength of the fundamental radiation. The probe beam travels along a second primary beam path 5 to the optical device 10, where both first and second beam paths 4, 5 are combined to a common beam path 3. A sample 301 to be investigated is arranged in the beam path 3, where it is subjected to the pump or probe beams, and a response of the sample is sensed with a detector device 340 as it is known from conventional pump-probe experiments.

According to further embodiments of the invention, other low-efficient nonlinear processes different from XUV generation, can be efficiently initiated inside an enhancement cavity, for example, low-order harmonics of the fundamental radiation, white light or difference frequency generation. They all can either be generated in a separate intracavity target or even in the optical relaying device 10 itself and then can be efficiently coupled out of the cavity by the optical relaying device 10. Additionally, a small portion of fundamental radiation can be coupled out collinearly with new spectral components giving thus new possibilities e.g. for pump-probe experiments. For the visible spectral range and beyond to IR, the reflection of new spectral components should be considered not only from the upper anti-reflection coating 12 of optical relaying device 10 as it was considered for XUV, but from the whole anti-reflection coating multi-layer structure. In our specific case fused silica as an upper layer of the anti-reflection coating starts to be transparent at around 150 nm. Above this wavelength interference between reflections from different alternating layers can not be neglected. The reflected light will be a result of the interference of the reflected light from all layers in multilayer anti-reflection coating.

The features of the invention disclosed in the above description, the drawings and the claims can be of significance both individually as well as in combination for the realisation of the invention in its various embodiments.

The invention claimed is:

1. A method comprising:
spatially relaying a first radiation component having a first wavelength in a range from UV to FIR wavelengths and a second radiation component having a second wavelength different from the first radiation component and within a range from 1 nm to 150 nm, wherein said relaying comprises splitting or combining the first and second radiation components using an optical relaying device which comprises: (a) a transparent plate comprising a material which is transparent for the first radiation component and (b) anti-reflection coatings on both side surfaces thereof, wherein the anti-reflection coatings have multilayer structures,
transmitting the first radiation component across the optical relaying device with predetermined incident and emergent angles, respectively, wherein said anti-reflection coatings are effective for the first radiation component at the incident and emergent angles, respectively, and
reflecting the second radiation component at the optical relaying device with a predetermined reflection angle being equal to at least one of said incident and emergent angles, wherein
the reflection angle is at least 75°, and
the first and second radiation components are split from each other toward different directions or combined into a common beam path.

2. The method according to claim 1, for splitting the first and second radiation components
the first and second radiation components are directed along a common primary beam path onto the optical relaying device, wherein the reflection angle of the second radiation component is equal to the incident angle of the first radiation component.

3. The method according to claim 2, wherein
the first radiation component is a fundamental radiation circulating in a resonator cavity and the second radiation component is a secondary radiation generated in the resonator cavity by an interaction of the fundamental radiation with a target medium.

4. The method according to claim 3, wherein
the resonator cavity is at least one of an active or passive enhancement cavity and a laser resonator.

5. The method according to claim 1, for combining the first and second radiation components
the first and second radiation components are directed onto the optical relaying device such that, after transmission and reflection, the first and second radiation components travel along a common secondary beam path, wherein the reflection angle of the second radiation component is equal to the emergent angle of the first radiation component.

6. The method according to claim 1, comprising at least one feature selected from the group consisting of:
the transparent plate is a plane-parallel plate, wherein the incident and emergent angles are equal,
the transparent plate is a wedged plate, wherein the incident and emergent angles differ from each other,
the transparent plate has a plane or a curved plate surface,
the transparent plate is made of fused silica, crystalline quartz, $CaF_2$, or synthetic quartz glass,
the anti-reflection coatings provide at least one of a polarization and wavelength filter,
the anti-reflection coatings have a predetermined dispersion adapted for pulse shaping of the first radiation component,
the anti-reflection coatings are adapted for polarizing of the first radiation component,
the anti-reflection coatings are made of $SiO_2$ and $Nb_2O_5$ layers, and
the transparent plate has an optical nonlinearity, such that additional spectral components are generated by an interaction of the first radiation component with the transparent plate.

7. The method according to claim 1, wherein
the first radiation component has a wavelength in a range from 800 nm to 1300 nm.

8. A method of out-coupling harmonic radiation from a resonator device, in particular an enhancement cavity or a laser resonator, comprising the steps of
generating second or higher harmonic radiation in the resonator device by an interaction of fundamental radiation with a target medium, and
separating the second or higher harmonic radiation from the fundamental radiation with the relaying method according to claim 1.

9. The method according to claim 8, wherein the resonator device includes a cavity section with two curved mirrors which define a focus position, where the target medium is provided, and wherein
the optical relaying device is arranged in the cavity section between one of the two curved mirrors and the focus position, or
the optical relaying device is arranged outside the cavity section with the two curved mirrors and the focus position.

10. An optical relaying device, adapted for spatially splitting or combining radiation components, comprising
a transparent plate, being capable of transmitting a first radiation component having a first wavelength in a range from UV to FIR wavelengths with predetermined incident and emergent angles, respectively, and further being capable of reflecting a second radiation component with a predetermined reflection angle being equal to at least one of said incident and emergent angles, said reflection angle being at least 75°, said second radiation having a wavelength different from the first radiation and within a range from 1 nm to 150 nm,
a first anti-reflection coating having a multilayer structure provided on a first side of the transparent plate, and
a second anti-reflection coating having a multilayer structure provided on a second side of the transparent plate, wherein
the first and second anti-reflection coatings provide anti-reflectivity for the first radiation component at at least one of the incident and emergent angles.

11. The optical relaying device according to claim 10, comprising at least one feature selected from the group consisting of:
the transparent plate is a plane-parallel plate, wherein the incident and emergent angles are equal,
the transparent plate is a wedged plate, wherein the incident and emergent angles differ from each other, the transparent plate has a plane or a curved plate surface, the transparent plate is made of fused silica, crystalline quartz, $CaF_2$, or synthetic quartz glass, the transparent plate has an optical nonlinearity, such that additional spectral components can be generated by an interaction of the first radiation component with the transparent plate, the anti-reflection coatings have a predetermined dispersion adapted for pulse shaping of the first radiation component, the anti-reflection coatings are adapted for polarizing of the first radiation component, the anti-reflection coatings are made of $SiO_2$ and $Nb_2O_5$ layers, and the anti-reflection coatings provide at least one of a polarization and wavelength filter.

12. A resonator device, comprising:

a plurality of cavity mirrors spanning a cavity beam path and including two curved cavity mirrors which are adapted for focusing a fundamental radiation component along the cavity beam path at a focus arranged for providing a target medium in the cavity beam path, and the optical relaying device according to claim 10.

13. The resonator device according to claim 12, further comprising an enhancement cavity device.

14. The resonator device according to claim 12, comprising a laser resonator.

15. The resonator device according to claim 12, wherein the curved cavity mirrors are arranged for an asymmetric focusing so that the focus is arranged with different path lengths from each of the curved cavity mirrors.

* * * * *